US009057879B2

(12) United States Patent
Knebel et al.

(10) Patent No.: US 9,057,879 B2
(45) Date of Patent: Jun. 16, 2015

(54) SPIM MICROSCOPE WITH A SEQUENTIAL LIGHT SHEET

(75) Inventors: Werner Knebel, Kronau (DE); Wolfgang Oestreicher, Mannheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 74 days.

(21) Appl. No.: 13/278,986

(22) Filed: Oct. 21, 2011

(65) Prior Publication Data

US 2012/0099190 A1  Apr. 26, 2012

(30) Foreign Application Priority Data

Oct. 22, 2010 (DE) .................. 10 2010 060 121
Jun. 15, 2011 (EP) ...................... 11169989

(51) Int. Cl.
  *G02B 21/18* (2006.01)
  *G02B 21/16* (2006.01)
  *G02B 21/00* (2006.01)
  *G02B 21/06* (2006.01)

(52) U.S. Cl.
  CPC .............. *G02B 21/16* (2013.01); *G02B 21/002* (2013.01); *G02B 21/06* (2013.01)

(58) Field of Classification Search
  CPC .... G02B 21/002–21/0076; G02B 21/06–21/16
  USPC ................................................. 359/368–395
  See application file for complete search history.

(56) References Cited

U.S. PATENT DOCUMENTS

| 5,731,588 | A | 3/1998 | Hell et al. |
| 7,554,725 | B2 | 6/2009 | Stelzer et al. |
| 7,787,179 | B2 | 8/2010 | Lippert et al. |
| 8,575,570 | B2 * | 11/2013 | Choi et al. ............ 250/459.1 |
| 2006/0033987 | A1 | 2/2006 | Stelzer et al. |
| 2009/0237765 | A1 | 9/2009 | Lippert et al. |
| 2010/0201784 | A1 | 8/2010 | Lippert et al. |
| 2010/0265575 | A1 * | 10/2010 | Lippert et al. ............ 359/385 |
| 2011/0031414 | A1 | 2/2011 | Lippert et al. |
| 2011/0036996 | A1 | 2/2011 | Wolleschensky et al. |

FOREIGN PATENT DOCUMENTS

| DE | 102007015063 | 10/2008 |
| DE | 102007045897 | 4/2009 |
| DE | 10 2008 009 216 | 8/2009 |
| DE | 102008018476 | 10/2009 |

(Continued)

OTHER PUBLICATIONS

A.H. Voie, et al: "Orthagonal-plane fluorescence optical sectioning: three-dimensional imaging of macroscopic biological specimens", Journal of Microscopy, vol. 170, 229-236 (1993).

(Continued)

*Primary Examiner* — Stephone B Allen
*Assistant Examiner* — James McGee
(74) *Attorney, Agent, or Firm* — Schlee IP International, P.C.; Alexander R. Schlee

(57) ABSTRACT

A SPIM-microscope (Selective Plane Imaging Microscopy) having a y-direction illumination light source and a z-direction detection light camera. An x-scanner generates a sequential light sheet by scanning the illumination light beam in the x-direction. By an illumination optics having a zoom optics that is provided in the beam path of the illumination light beam the focal length of the illumination light beam can be varied.

22 Claims, 7 Drawing Sheets

(56) References Cited

FOREIGN PATENT DOCUMENTS

| | | |
|---|---|---|
| GB | 2416453 | 1/2006 |
| WO | 9502139 | 1/1995 |
| WO | WO 2004053558 A1 * | 6/2004 |
| WO | 2009124700 | 10/2009 |
| WO | 2010069987 | 6/2010 |

OTHER PUBLICATIONS

J. Huisken, et al.: "Optical Sectioning Deep Inside Live Embryos by Selective Plane Illumination Microscopy", Science, vol. 305, 1007-1009 (2004).

S. Hell, J. Wichman: "Breaking the diffraction resolution limit by stimulated emission: stimulated-emission-depletion fluorescence microscopy", Optics Letters vol. 19 (11), 780-782.

F. Fahrbach, A. Rohrbach: "Microscopy with non diffracting beams", FOM 2009, Krakau (Abstract).

J. Huisken, D.Y.R. Stainier: "Even fluorescence excitation by multidirectional selective plane illumination microscopy (mSPIM)", Optics Letters, vol. 32, No. 17, 2608-2610 (2007).

J. Sharpe, et al., "Optical Projection Tomography as a Tool for 3D Microscopy and Gene Expression Studies", Science 296: 541-545 (2002).

* cited by examiner

SPIM MICROSCOPE WITH A SEQUENTIAL LIGHT SHEET

CROSS-REFERENCE TO RELATED APPLICATION

This application claims the priority of the German patent application DE 102010060121.7 having a filing date of Oct. 22, 2010 and claims priority of the European patent application EP 11169989.8 having a filing date of Jun. 15, 2011. The entire content of this prior German patent application DE 102010060121.7 and European patent application EP 11169989.8 is herewith incorporated by reference.

BACKGROUND OF THE INVENTION

The invention relates to a SPIM-microscope comprising a light source sending an illumination light beam from a y-direction onto an object to be imaged and a camera detecting in a z-direction as a first detection direction light emanating from the object as fluorescent light and/or as reflected light, wherein the z-direction extends substantially perpendicular to the y-direction.

In particular, biological samples should be analyzed both quickly and without damaging the sample. For many applications, it is useful to generate a 3-dimensional image. Scattering artifacts and absorption artifacts should be avoided that may occur due to interaction of the illumination light with the sample, in particular in the field of fluorescence microscopy where the illumination light has the function of an excitation light for exciting fluorescence.

For analyzing microscopic samples fast, without causing damage and with a high resolution the so-called SPIM technology is specifically suitable (Selective Plane Illumination Microscopy) where the illumination light generates a light sheet, while the detection light generated by fluorescence and reflection is detected in a perpendicular direction compared to the illumination direction by a camera.

A light sheet is an illumination volume with a substantially rectangular cross-section that is very thin in a first cross-sectional direction (here the z-direction) and significantly larger in a second cross-sectional direction (here the x-direction) in comparison to the first cross-sectional direction. The illumination direction (here the y-direction) extends substantially perpendicular to the first cross-sectional direction (here the z-direction) and substantially perpendicular to the second cross-sectional direction (here the x-direction). The light sheet is focused by a cylindrical lens and the focus or a focal length of the light sheet is to be understood as a certain range that extends in the illumination direction (here the y-direction) where the light sheet is particularly thin so that the illuminated volume has the shape of a sheet, i.e. is very thin in the z-direction and much larger in the x- and in the y-direction.

Generating a light sheet according to the prior art SPIM technology using a cylindrical lens has the disadvantage that the system is quite unflexible, for instance provides a fixed focus and therefore a predetermined illuminated volume. For achieving a high resolution, a very thin and long focus is advantageous. This focus can be scanned for obtaining a 3-dimensional image in one direction over the sample. Since an increased length also increases the width the resolution in the z-direction is decreased. This means that a long focus at a low numerical aperture of the illumination optics has the consequence that also the thickness of the illuminated volume is high. This means that the optical resolution along the optical axis in the detection direction is likewise low.

By interaction of the excitation light with the sample scattering artifacts and absorption artifacts are generated which are visible as striations or shadows in the image along the illumination axis, which is also referred to as "Curtain-Effects".

One prior art approach for reducing the curtain-effects is the mSPIM-technology according to which in addition in the telecentric arrangement by means of a resonant mirror the light sheet is tilted in relation to the optical axis so that the illumination light beam incidents from a variety of direction's onto the sample, resulting in reducing the scattering artifacts and absorption artifacts. In simple terms, varying the incident direction provides some background illumination for the absorbing areas within the sample so that the striations or shadows in the image are reduced. A disadvantage of this technology is the additional complexity, in particular if the light sheet should be scanned in the z-direction for generating a 3-dimensional image. Apart from that, this still does not solve the problem of the low flexibility due to the predetermined focus.

SUMMARY OF THE INVENTION

It is an object of the invention to increase the flexibility of the microscope described at the outset and at the same time achieve a higher resolution and detect more image data.

According to the invention, this is achieved by an x-scanner generating a sequential light sheet by scanning the illumination light beam in an x-direction, wherein the x-direction extends substantially perpendicular to the y-direction and to the z-direction and the light sheet is sequentially formed in a plane that is defined by the x-direction and the y-direction; and by an illumination optics comprising a zoom optics provided in a beam path of the illumination light beam, the zoom optics being adapted to change the focal length of the illumination light beam.

DETAILED DESCRIPTION OF THE INVENTION

According to a preferred embodiment of the invention, a photodetector is provided detecting detection light sent from the object in the opposite direction of the y-direction as a second detection direction, the detection light being fluorescent light and/or reflected light. This generates a second data stream that can for instance be used in addition for generating an image confocally. This optional additional image can be switched on or off as desired.

When using multiphoton lasers, confocal detection as well as the non-descanning light path can be chosen for generating images by multiphoton detection. The non-descanning detection path has the advantage of providing a higher collection efficiency, specifically in case of thick samples. The term non-descanning should be understood as coupling out detection light directly at the detection objective.

If the SPIM detection beam path (in z-direction) is used for collecting the fluorescent light and the light is a directed into a photomultiplier or an APD or APD array, a much higher efficiency is achieved than by using the illumination optics for collecting the fluorescent light since typically the used numerical aperture of the illumination system is lower than the numerical aperture of the detection system of the SPIM arrangement.

According to a further preferred embodiment of the invention, in parallel to the 2-dimensional wide field image generated by the SPIM-technology also confocally, optionally by using a multiphoton illumination, a 1-dimensional image of the object is generated that comprises a line extending in the x-direction. In this case, the 2-dimensional image images that illumination layer that is illuminated by the light sheet and as described above is influenced by the zoom optics, while in parallel a so-called x-t-image is generated, that means a line image that may in particularly in biological samples provide information about the velocity of movement of specific elements within the object, for instance provide information about the diffusion of molecules or other cell parts (organelles).

Preferably, for generating a 3-dimensional image, a first z-scanner is provided moving the object in the z-direction so that sequentially a plurality of light sheets spaced in z-direction with respect to each other are generated in the respective illumination planes, wherein a distance between the respective light sheets and the camera remains unchanged. An advantage is that the entire illumination optics as well as the SPIM detection optics and the confocal detection optics that can optionally be switched on in addition can remain at the same location and in addition the illumination beam does not need to be deflected in the z-direction by a scanner, therefore simplifying the illumination optics. In the alternative, it is also possible to move the illumination optics or to deflect the illumination beam, for instance by means of an Acousto Optical Deflector (AOD) or by means of a galvanometer. In this case, it is preferable to have the SPIM detection optics tracking behind, which can be accomplished by changing the position of the objective of the SPIM detection optic or in the alternative by moving the entire SPIM detection optics including the camera.

According to another preferred embodiment of the invention, an image processing unit is provided that combines the sequentially generated images correlating to the respective plurality of light sheets which are spaced in the z-direction in a distance to each other to a 3-dimensional image.

According to another preferred embodiment of the invention, in parallel to the 3-dimensional image generated by the SPIM-technology also confocally a 2-dimensional image of the object is generated in a plane defined by the x-direction and the z-direction.

According to another preferred embodiment of the invention, a second z-scanner is provided moving the illumination light beam in the z-direction in relation to the object for generating sequentially a plurality of light sheets spaced in the z-direction with respect to each other, and a third z-scanner is provided that tracks the detection beam path according to the deflection of the illumination light beam in z-direction by the second z-scanner so that a distance between the light sheet and the camera remains unchanged. The data stream generated in this fashion is preferably processed by an image processing unit that combines the sequentially generated images correlating to the respective plurality of light sheets which are spaced in the z-direction in a distance to each other to a 3-dimensional image by a variety of possible Rendering methods (Projection, Transparent, Shading, Ray Tracing etc.). Preferably, in addition to the 3-dimensional image that is generated by rendering, in parallel to the 3-dimensional image generated by the SPIM-technology also confocally (multiphoton) a 2-dimensional image of the object is generated in a plane defined by the x-direction and the z-direction.

If a larger area of the object should be imaged, this can be accomplished by so-called "Stitching", i.e. combining the sequentially imaged adjacent object areas. For this purpose, the object is moved in the x-direction and a new area is illuminated and the image detected by a camera. The number of movements in the x-direction depends on the size of the object, the size of the field of the objective, and the camera parameters. It is also possible to move the object in the y-direction for detecting a larger area of the object. All of these images can be combined into one large overall image.

By a flexible optical zoom arrangement the size of the light sheet (in the y-direction and in the z-direction) can be adjusted.

If it is desired to illuminate only a thin layer, the numerical aperture of the zoom optics is increased, having the consequences of decreasing the usable size of the light sheet.

By sequentially detecting images along the y-direction (Stitching) sequences of images can be detected that have an increased resolution along the z-direction.

Since the optical parameters of the zoom optics are known, by choosing suitable image processing only those areas can be used and combined that provide the increased resolution.

The zoom optics allowing varying the focal length of the illumination light beam can be an optical zoom according to a preferred embodiment of the invention, having lens groups which are mechanically moved with respect to each other. By the zoom optics in combination with the illumination objective the focal length of the illumination light beam can be expanded or shortened by changing the numerical aperture, allowing expanding or shortening the length of the field that is illuminated by the light sheet in the y-illumination direction.

According to another preferred embodiment, an electronic zoom is provided that is adapted to change the scanning length in the x-direction. Preferably, the number of image pixels in x-direction is maintained unchanged by the electronics zoom independently of the scanning length in x-direction that has been selected. If the scanning length in the x-direction is reduced, but the number of scanned pixels is kept unchanged over that shorter scanning length, the resolution can be increased in case of a confocal detection up to reaching the Nyquist Theorem.

If simultaneously a confocally detected image is generated, it is noted that also this image comprises a higher resolution up to reaching the Nyquist Theorem in the x-direction but at a smaller size of the image in the x-direction, which has the function of an electronic zoom.

According to a preferred embodiment of the invention, an electronic zoom is provided in addition by which the scanning length in the z-direction can be changed along which a plurality of spaced apart light sheets are generated sequentially. In this case, substantially the same as for the electronic zoom acting in x-direction applies. Preferably, the number of light sheets which are spaced with respect to each other in the z-direction is maintained unchanged by the electronics zoom independently of the scanning length in the z-direction that has been selected.

According to another preferred embodiment, the illumination light beam scanned in the x-direction is turned off at or close to the return point where the maximum scanning length in x-direction has been reached. This allows avoiding damage to the sample since less light is sent onto the sample at the return points. In addition, this also avoids that the image appears to be specifically bright at the return points since the illumination is maintained for a longer period of time at the return points in comparison to other areas of the sample. In the ideal case, the scanning velocity in x-direction follows a saw-tooth graph. If the scanning velocity is very high, this is, however, difficult to accomplish so that instead a sinus graph is chosen, resulting at the return points in a slower scanning velocity than in the middle of the scanning path. In particular for sinus curves it is useful if the illumination beam is turned off near the return points.

According to another preferred embodiment of the invention, the camera is an area detector chosen from the group consisting of CMOS-camera, CCD-camera or array-detectors. Since the SPIM technology is a wide field microscopy technology, the camera should provide a localization of the detection light.

According to another preferred embodiment of the invention, the microscope according to the invention is provided with a switch adapted to switch between the following operational modes: confocal detection of detection light opposite to the y-illumination direction; SPIM-detection of wide field detection light in the z-direction; and simultaneous detection of the aforementioned confocal detection and SPIM-detection.

According to another preferred embodiment of the invention, a deactivation light source is provided sending from the y-direction a deactivation light beam onto the object making the sequentially generated light sheet in the z-direction thinner, wherein the deactivation light beam is sent offset in the z-direction onto the object in relation to the illumination light beam and extends in parallel to that illumination light beam that is scanned in the x-direction. Preferably, the cross-section of the deactivation light beam has been modulated such that it comprises two maxima that are provided as is viewed in the z-direction in front and behind the center of the excitation beam in which center the excitation beam has a zero point in between the maxima. It is, however, in the alternative also possible to send two separate laser beams as deactivation beams, or to make the light sheet only on one side thinner, i.e. as viewed in the z-direction, to provide only one deactivation beam in front of the excitation beam or behind the excitation beam.

According to another preferred embodiment of the invention an excitation light beam modulator is provided that is adapted to modulate the excitation light beam into a Bessel beam. A Bessel beam comprises an inhomogeneous intensity distribution over the beam cross-section, comprising a relatively sharp main maximum and several significant side lobes. In particular when adding a STED deactivation beam, the side lobes can be suppressed by deactivation, so that only a narrow main maximum in the center of the excitation beam remains. A Bessel beam further has the advantage to reform behind a relatively opaque section at least partially so that curtain-effects are decreased further.

According to another preferred embodiment of the invention, the illumination light source is a pulsed laser; the illumination light beam is a multiphoton laser beam; and a multiphoton signal is detected in the z-direction. The specific advantage is that the SPIM detection optics has a bigger numerical aperture and therefore provides for a higher signal strength detection for detecting the multiphoton signal.

According to another preferred embodiment of the invention the camera is a fast camera that is adapted to detect in addition to the SPIM signal also the multiphoton signal. Fast cameras can for instance detect up to 1000 images per second in a format 512×512.

According to another preferred embodiment of the invention, a switchable mirror is provided, allowing extracting the multiphoton signal from the z-direction and directing it to a photodetector. Photodetectors are generally faster than cameras, but provide no localization, which, however, is not absolutely necessary if a localization can be provided via the multiphoton illumination beam, which is in particular easy to accomplish in case of a multiphoton illumination since for this type of illumination it is known which small volume within the object is illuminated at a specific point in time, so that for detecting the signal the light coming from all direction scan be detected.

BRIEF DESCRIPTION OF THE DRAWINGS

The invention is discussed in the following by referring to the drawings. In the drawings show.

DETAILED DESCRIPTION OF THE DRAWINGS

Figure 1:
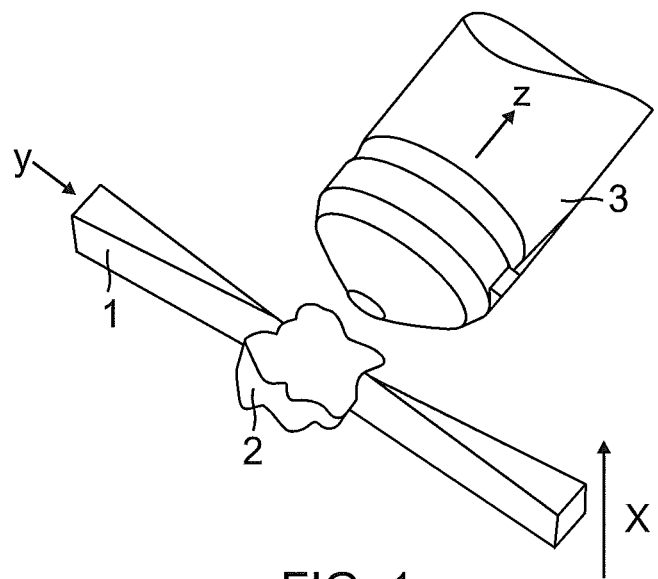
FIG. 1 a schematic perspective view of the basic principle of the SPIM-technology according to the prior art.

FIG. 1 shows in a simplified fashion the principle of a SPIM-microscope according to the prior art, operating based on the "Selective Plane Imaging" technology principle. Illumination is performed in the y-direction by a light sheet for illuminating the object in a specific object plane. The detection direction extends substantially perpendicular to the light sheet 1, i.e. in z-direction, wherein the detection of the detection light is performed by an objective 3. As shown in FIG. 1, the light sheet 1 should be specifically thin over a range of the inner section for obtaining a high a resolution in the z-direction. A high resolution is accomplished if the light sheet 1 comprises a narrow focus within the object.

As will be explained below in more detail, the length of this focus can be influenced, making the imaged field larger, but decreasing the sharpness of the focus and therefore decreasing the narrowness of the light sheet 1 and therefore decreasing the resolution of the picture in the z-direction. Depending on the specific application, it might be useful to have less resolution in the z-direction but at the same time view a larger field and a larger imaging volume based on a thicker light sheet. A larger imaging volume might also be useful if the generated image still allows to view the aspects of interest of the image well, but at the same time allows for a larger imaging volume having the advantage that it is easier to ascertain that the imaged volume does indeed contain the aspect of interest. If an image of an even higher resolution should then be generated of the aspect of interest it is possible to manipulate the focus of the sequential light sheet 1 by the zoom-optics to make the focus smaller but sharper.

In contrast to confocal scanning microscopy, detection of the detection light in the z-direction according to the SPIM-technology requires localization of the detected light since the SPIM-technology is a wide-field microscopy technology. The localization is typically accomplished by a camera, for instance a CCD-camera or a CMOS-camera. If a 3-dimensional image of an object should be generated by the SPIM-technology, the light sheet 1 can be scanned in z-direction and the images obtained in the various illumination planes can be combined to generate a 3-dimensional image. This image processing is also named "Rendering", in this case in the z-direction.

Figure 2:
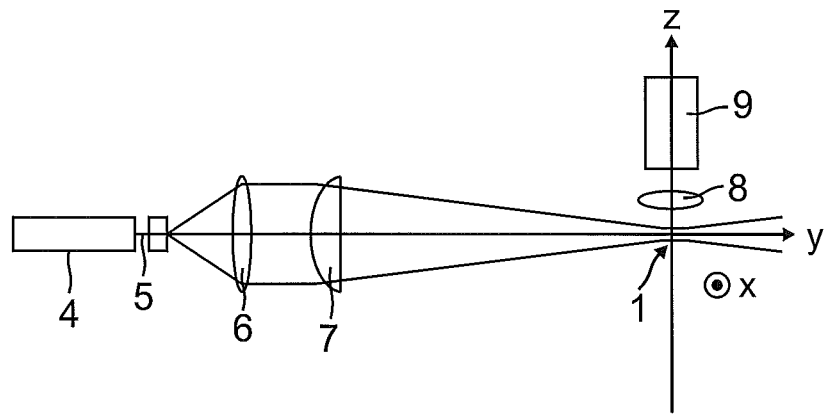
FIG. 2 a schematic view of the illumination beam paths and the detection beam paths according to the SPIM-technology according to the prior art.

FIG. 2 shows schematically an illumination beam path according to the prior art in a SPIM-microscope. A laser 4 generates an illumination beam 5 that is sent through a beam expander into the collimating lens 6 that is succeeded by a cylindrical lens 7 focusing the light sheet 1 onto the object. An objective lens collects the detection light and directs it into a camera 9. The focus of the light sheet can be influenced by moving elements in the group of lenses, in this strongly simplified example according to FIG. 2 by moving the cylindrical lens 7 in relation to the collimating lens 6.

Figure 3:
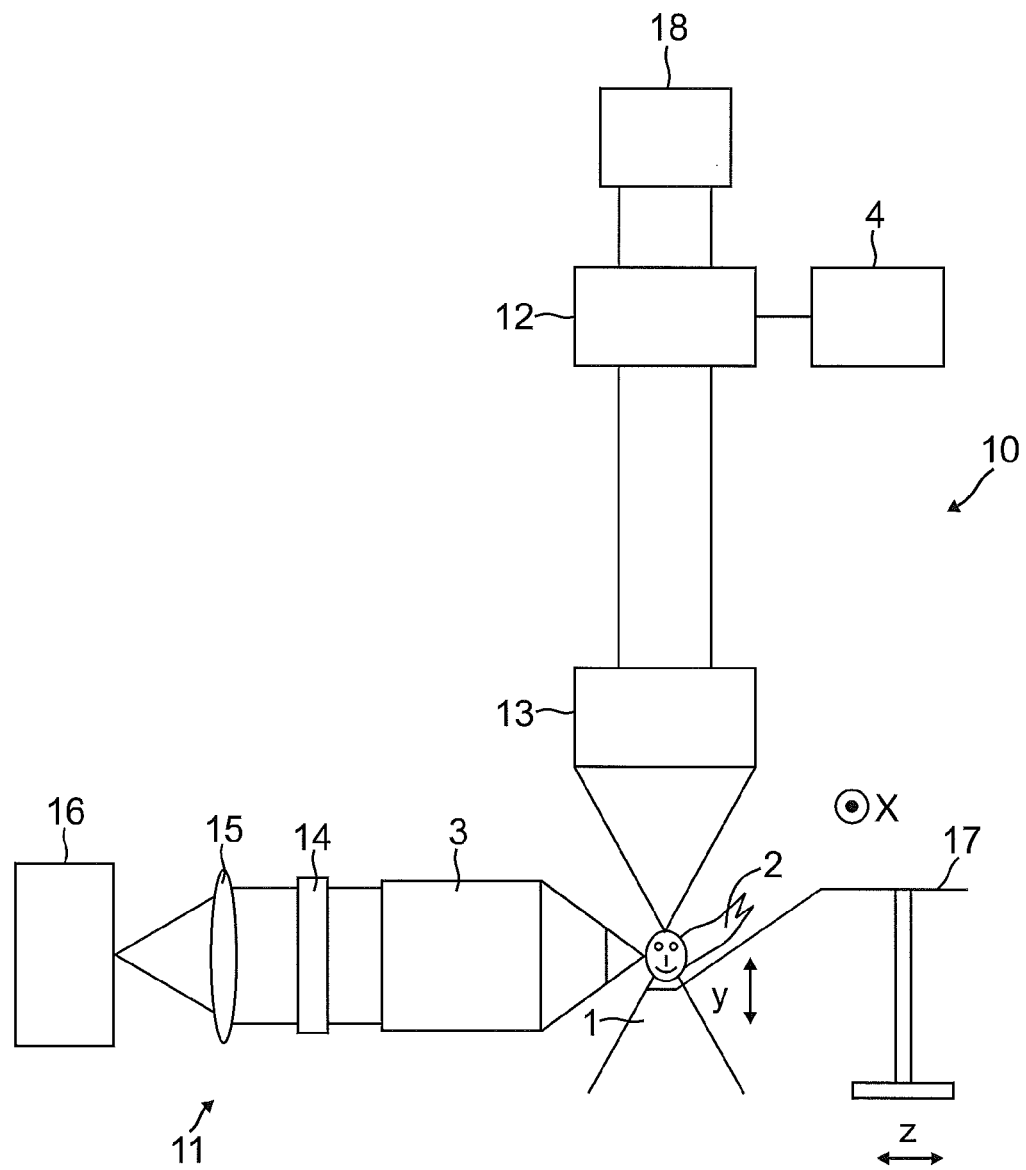
FIG. 3 a schematic view of the microscope according to the invention.

FIG. 3 shows the schematic structure of the SPIM-microscope according to the invention, having an illumination beam path denoted by reference numeral 10 and a SPIM-detection light beam path denoted with the reference 11. The illumination optics beam path 10 comprises in addition the function of a confocal detection light beam path, but extending in the opposite direction compared to the illumination direction.

First of all, the illumination optics beam path is described; a laser 4 generates illumination light that is sent via a scanner 12 into the zoom optics 13. The scanner 12 generates a sequential light sheet 1 for illuminating the object 2. For sequentially generating the light sheet 1 the illuminating laser beam is scanned in the x-direction, i.e. according to FIG. 3 out of the drawing plane or into the drawing plane, respectively. The laser beam may for example have a circular cross-section, but may in the alternative also be modulated in its cross-sectional shape, for instance have an oval cross-section, wherein the longer axis of the oval cross-section extends in the x-direction. Likewise, the illumination beam path can for example be rectangular or may have any other optional shape.

The SPIM-detection light beam path 11 extends in the z-direction, i.e. substantially perpendicular to the y-direction in which the illumination beam path 10 extends. It may be advantageous to deviate slightly from the perpendicular relationship between the illumination beam path and the detection beam path, for instance smaller or larger angles than 90° between the two beam paths can be chosen, for instance for creating background illumination for parts or particles within the object. It is also possible to detect images from different angles and then combine these, as for instance known as mSPIM technology. In the following, for keeping the description simple, a rectangular relationship is described, but should be understood as also encompassing deviating angles which are however to be understood as more or less close to 90°. The detection light emanating from the object 2 either due to reflection or fluorescent light emission is collected by the objective 3. Particularly for multi-color detection a color filter 14 is provided downstream of the objective and is capable of filtering out detection light of specific wavelengths which is then directed via a tubular lens 15 to a camera 16, for instance a CCD-camera 16.

For generating a 3-dimensional image the object carrier 17 can be scanned in the z-direction for illuminating sequentially different illumination planes within the object 2, each of the illumination planes being scanned by a scanned laser beam that is scanned in the x-direction and therefore illuminated by a sequentially formed light sheet 1 that is sequentially formed in the respective illumination plane. A plurality of in the z-direction adjacent sequentially formed light sheets 1 can be combined by "Rendering" in the z-direction.

In case 3-dimensional images should be generated by "Rendering" with a z-drive, moving the object 2 has the advantage that the distance between the respective adjacent illumination planes within the object and the objective remains the same since neither the location of the illumination beam is changed nor the location of the camera 16. In the alternative it is possible to scan the light sheet 1 in z-direction, for instance by a galvanometer. This requires though that the objective 3 is also moved so that the distance between the respective illumination plane and the object remains the same. In the alternative, it is of course possible to move the entire SPIM detection optics comprising the objective 3, the filter 14, the tubular lens 15 and the camera 16.

The illumination detection optics beam path 10 may as already mentioned further have the function of a confocal detection light beam path, for which purpose the detector 18 can be provided detecting light reflected from the object in the y-direction and/or detecting emitted fluorescent light. Simultaneously with image detection via the SPIM technology through the detection light beam path 11 it is also possible to perform confocal image detection in parallel since the light sheet 1 is generated sequentially by scanning in the x-direction. The confocally generated image is one dimension lower compared to the image detected by the SPIM-detection. If for instance only a 2-dimensional image is generated by the SPIM-detection, i.e. an image within only one single image plane, it is also possible to detect a so called x-t image, i.e. a 1-dimensional line image. This can for instance be used for determining the diffusion speed of specific molecules, that may be marked by a marker or are dyed for emitting fluorescent light, while the 2-dimensional SPIM-image that is imaged simultaneously may provide different information, for instance information which molecules combine to which other molecules in the imaged imaging plane of the object.

The same applies if by means of the SPIM-detection a 3-dimensional image with a z-drive is generated, i.e. that a confocal 2-dimensional image is generated. In this fashion it is for instance possible to determine which molecules combine within the object in the 3-dimensional shape with which other molecules, while in parallel the diffusion speed of molecules diffusing through specific planes can be determined. The simultaneous detection of a SPIM-image with the dimension "n" and a parallel confocally generated image with the dimension "n−1" allows in combination additional determinations, for instance the additional speed information allows to determine which individual elements, for example molecules or other elements, move within the object 2. In particular in the field of microscope this finds new applications within living organisms.

Figure 4:
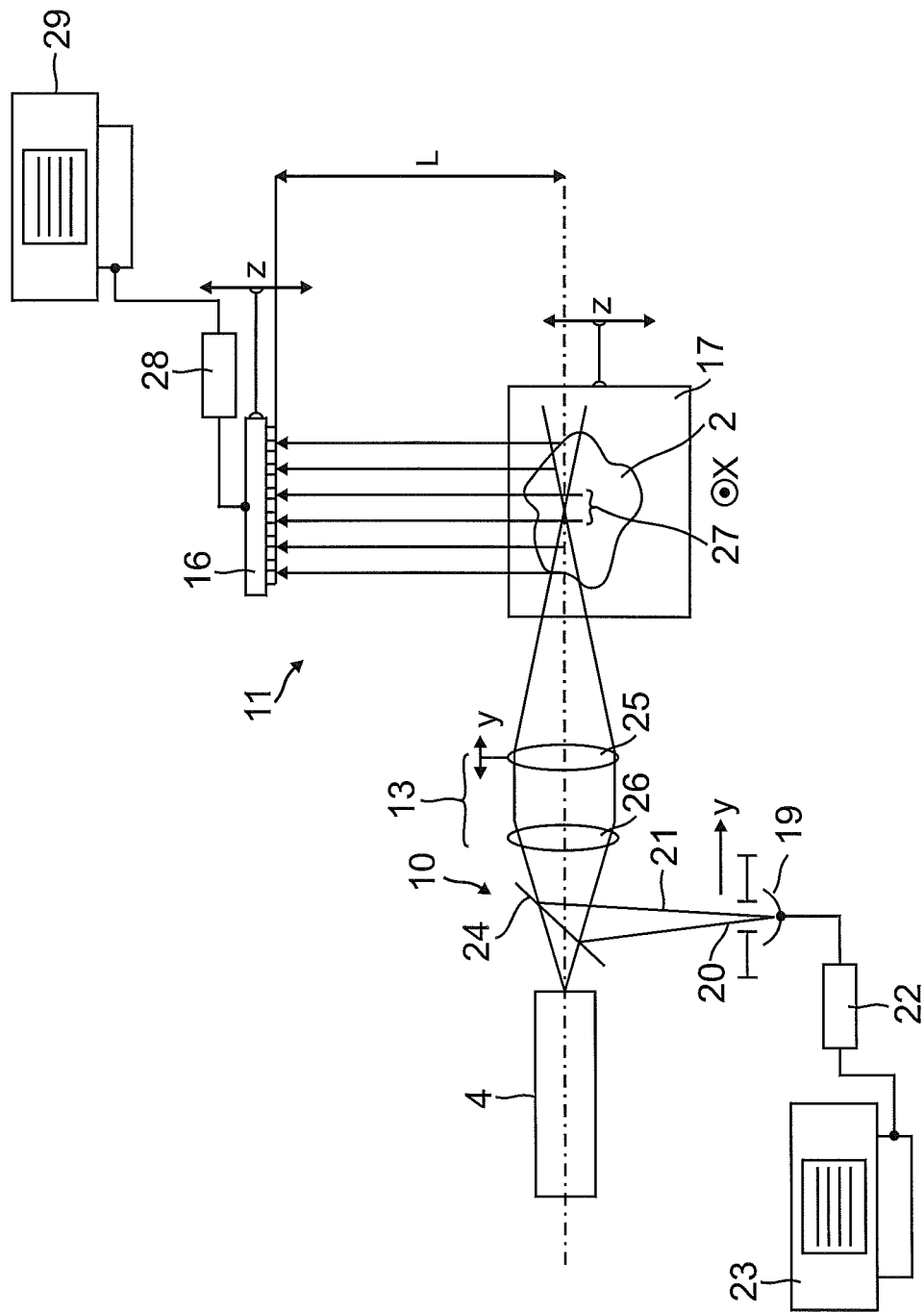
FIG. 4 a schematic view of the microscope according to the invention as shown in FIG. 3 but viewed in the x-scanning direction, including the illumination beam path and the detection beam path.

FIG. 4 shows an additional embodiment of the invention. Similar elements are designated with the same reference numerals as in the preceding figures. Also in this figure the SPIM detection light beam path is denoted by the reference numeral 11, while the illumination beam path is designated with the reference numeral 10. Also in this embodiment according to FIG. 4 the illumination beam path 10 has the function of the additional detection beam path wherein the signal detection is performed by means of a photodiode 19 receiving through an aperture 20 confocally detection light 21, and sends a respective signal via the image processing unit 22 into a monitor 23. The detection light is deflected by dichroic mirrors 24 to a photodiode 19. Instead of the photodiode 19 also other light sensors, for instance Avalanche diodes, photomultipliers or a camera can be provided. Since this relates to confocal image detection, no localization is necessary since the information about the location comes from the scanned illumination beam, i.e. it is known which image point of the object is illuminated at a specific point in time, and therefore the information is known that the signal received from that specific image point is from that image point that has been illuminated immediately prior to receiving the signal. Therefore, the expenditure for a camera is not necessary for confocal detection.

For changing the focus of the sequentially generated light sheet 1 a zoom lens 25 may be moved in the y-direction in relation to a further lens 26. For practical applications, a lens group will be provided for this purpose, however, for simplification the discussed embodiment is demonstrated with only 1 single zoom lens 25. The zoom optics 13 in combination with the illumination objective (macro objective) therefore provides an optical zoom allowing to modify the length of the focus range 27. For simplification, the details of the SPIM-detection optics have been omitted in FIG. 4, as these optics have already been shown in FIG. 3 comprising the objective 3, the filter 14 and the tubular lens 15. The schematically shown CCD-camera 16 provides for localization station in the x-y-plane for the detection light received in the z-direction. Via the SPIM image processing unit 28 the signals received by the CCD camera are processed and forwarded to the SPIM monitor 29. If a number of planes should be illuminated within the object 2 the object carrier 17 can be moved in the z-direction. As it can be clearly understood from the illustration according to FIG. 4 the length L meaning the distance between the illumination plane and the CCD-camera always remains the same. As already explained in connection with FIG. 3, it is also possible to move the illumination beam in z-direction while keeping the object 2 at the same location, and by moving instead the CCD-camera, or as this might be easier to implement, to change the position of the objective 3 in relation to the CCD camera 16.

Figure 5:
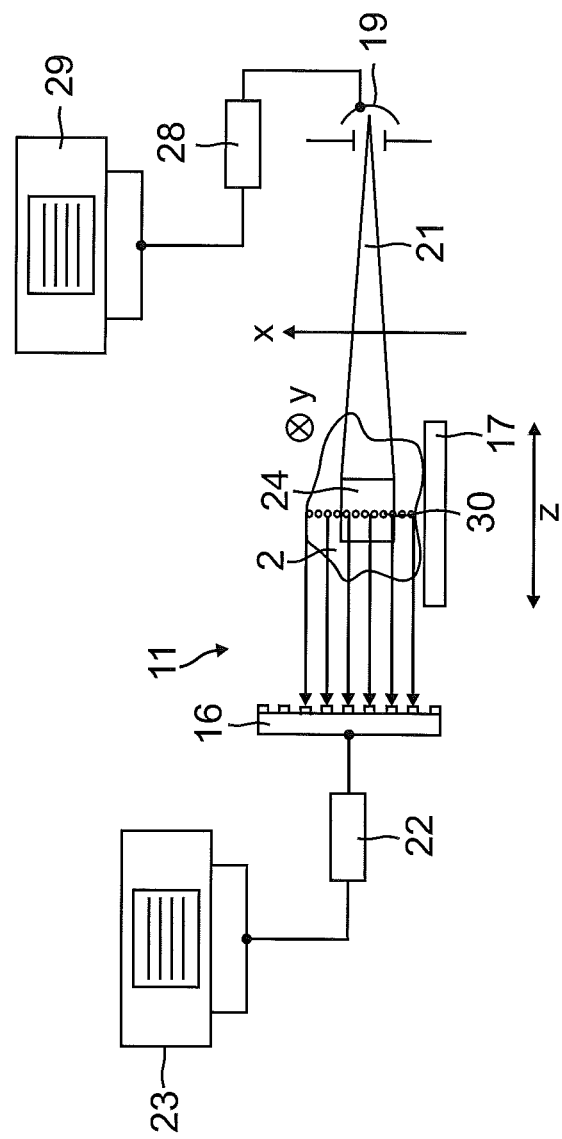
FIG. 5 a schematic view of the microscope shown in FIG. 4, but viewed in the y-illumination direction.

FIG. 5 shows the embodiment illustrated in FIG. 4, but as viewed from a different viewing point, namely in direction of the illumination beam, i.e. viewed in the y-direction. Illustrated are here in particular the individual image points 30 which are scanned in the x-direction for generating a sequentially formed light sheet 1. The dichroic mirror 24 deflects the detection light in direction of the photodiode 19. The object carrier 17 can be scanned in the z-direction, i.e. can be moved towards the CCD-camera 16 or moved away from the CCD-camera for illuminating different illumination planes within the object.

Figure 6:
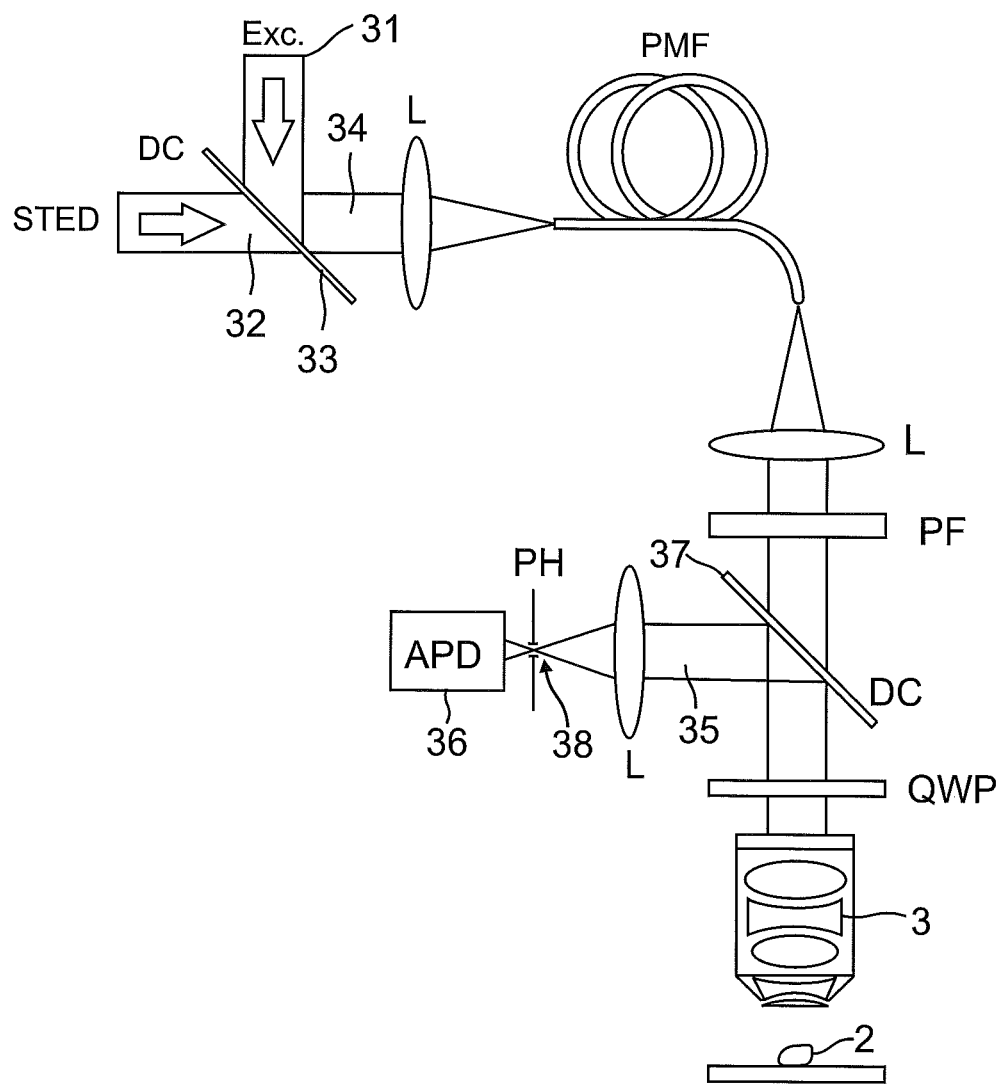
FIG. 6 a schematic view that also demonstrates the STED-principle according to the prior art.

In a further preferred embodiment, the light sheet 1 can be narrowed further by applying STED (Stimulated Emission Depletion), i.e. can be made thinner for accomplishing a higher resolution in the z-direction. The basic structure of a STED microscope as it is known from the prior art is shown in FIG. 6. An excitation beam 31 and a deactivation beam 32 are combined by a beam combiner, in this embodiment for example by a dichroic filter, to a joint beam path 34 that is directed through an objective 3 onto the object 2. Several other optical elements can be provided in between, for instance lenses, light conducting fibers or color filters. The deactivation beam is typically modulated in its intensity distribution, which can for instance be accomplished by phase plates, but also by lenses specifically structured for that purpose. The modulation can be performed in that the deactivation beam has a zero point in the middle, meaning that the intensity is zero or very low in the zero point while around this zero point a uniform, ring-shaped intensity maximum is provided. The dyes which are used in fluorescence microscopy react on specific excitation wavelengths and deactivation wavelengths allowing to excite fluorescence or to deactivate fluorescence specifically well. Typically, an excitation wavelength and a deactivation wavelength differ from each other and the excitation beam and the deactivation beam are sent in a time-delayed manner with respect to each other onto the object. By exciting, an image point of a specific size can be excited to emit fluorescent light, while immediately thereafter around the center of excitation a deactivation can be applied, allowing to narrow down the fluorescent light emitted from this image point of the object 2 to a small image point and therefore allowing to increase the resolution. For multi-color fluorescence microscopy a variety of different dyes can be used distinguishing from each other by different excitation wavelengths, i.e. excitation light of a variety of wavelengths that allow a specifically strong excitation for emitting fluorescent light.

Preferably, the combination of dyes can be chosen such that these can be deactivated by a common, same deactivation wavelength so that it can be avoided having to provide a variety of deactivation wavelengths.

The detection light 35, which is sent from the object back through the objective 3, can be sent by a beam splitter, in this case likewise a dichroic mirror 37, through a lens and a suitable aperture 38 for eliminating scattered light onto a photodetector 36.

Figure 7:
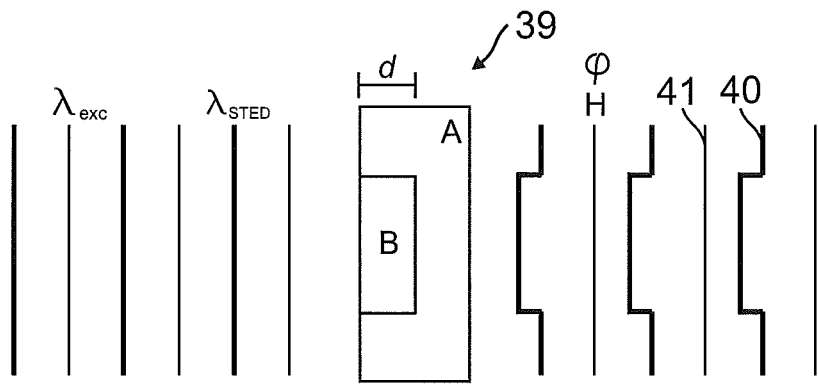
FIG. 7 is schematic view demonstrating the modulation of the STED-deactivation beam by a phase plate.

Modulation of the deactivation beam 40 by a phase plate 39 is demonstrated in FIG. 7. Both the phase as well as the intensity distribution can be modulated with such phase plates 39. For this purpose, the phase plate is designed such that the deactivation beam 40 is modulated, but not the excitation beam 41, i.e. the modulation depends on the wavelength which differs for the deactivation beam 40 in comparison to the excitation beam 41.

It is to be understood that the STED-principle can also be implemented in the illumination beam path 10, as demonstrated in FIG. 4. In addition to the laser 4 for the illumination light, which in this case is equal to the excitation light, another laser can be provided for generating the deactivation light. An excitation beam and a deactivation beam can either be combined into one beam path, as shown in FIG. 6, or the deactivation beam can be sent along a separate beam path. It would also be possible to generate the excitation beam and the deactivation beam with only one single laser 4 (white light laser). For this purpose, the beam is split to send one part of the beam through an Acousto Optical Element as for instance an Acousto Optical Tunable Filter (AOTF) where the desired wavelength can be selected. By using pulsed lasers a time delay between the excitation beam and the deactivation beam can be implemented by a so-called delay stage.

Figure 8A:
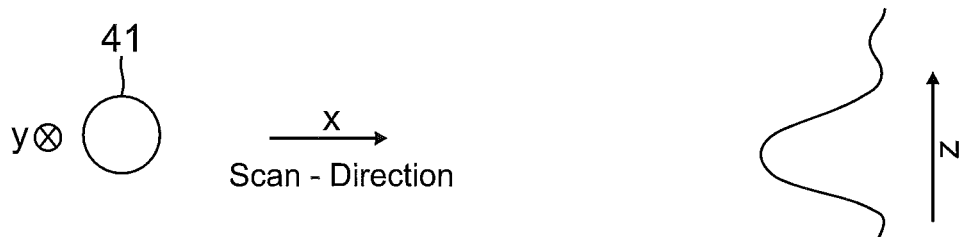
FIG. 8a the cross-section of an excitation beam as well as the related intensity distribution with the coordinates x, y and z.
Figure 8B:
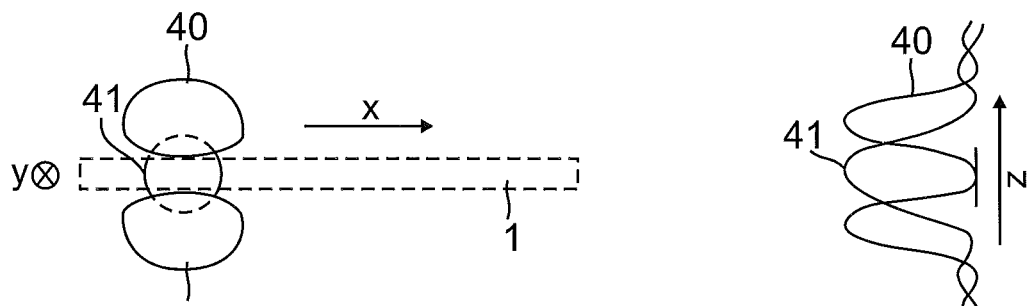
FIG. 8b the excitation beam plus the deactivation beam compared to each other as well as the sequential light sheet generated by scanning in x-direction together with the related intensity distribution with the coordinates x, y and z.

One embodiment of the invention is shown in FIGS. 8a and 8b. FIG. 8a shows the cross-section of a circular excitation beam 41. The directions x, y and z, as shown in FIGS. 4 and 5, are also shown in the FIGS. 8a and 8b. An intensity distribution profile of the excitation beam is shown on the right side, and typically follows a Gauss distribution—apart from relatively small side lobes due to diffraction. FIG. 8b shows a deactivation beam 40 that is modulated such that it comprises on both sides of the deactivation beam 41 an intensity maximum with a zero point in between where the intensity is zero or at least very low. As it can be seen in FIG. 8b, the intensity maxima of the deactivation beam 40 which intensity maxima are provided on both sides of the zero point do not have a circular cross-section, but comprise a cross-section having a flattened curvature towards the center in comparison to the side facing away from the excitation center. As the sequentially generated light sheet 1, which is demonstrated in FIG. 8b in interrupted lines, only a small band in the center area remains in which the deactivation light does not deactivate fluorescence. At the right side next to the cross-section of the excitation beam 41, deactivation beam 40, and sequentially generated light sheet 1, the intensity distributions of the excitation beam 41 and the deactivation beam 40 are demonstrated in FIG. 8*b*.

The STED-deactivation beam can be selectively in addition turned on or it can be turned off, which can also be performed just per line or per pixel in x-direction. Since the information is known when the deactivation beam is turned on or is turned off, the respective data streams can be separated, i.e. into a first data stream for generating an image based on the thicker light sheet and respectively covering a larger illumination area (compared to the cross-section of the illumination focus) and a larger illumination volume, and a second data stream for generating an image based on thinner light sheets with a smaller illumination area (in relation to the cross-section of the illumination focus) and a smaller illumination volume. This allows to generate simultaneously in the z-direction a high resolution image by adding the STED-beam, and in z-direction an image of a lower resolution without adding the STED-beam, but with the advantage of illuminating a larger volume within the object.

Independently of adding or turning off the STED-beam, this microscope allows to generate in parallel simultaneously a SPIM-microscopy image of the dimension n and a confocally generated image of the dimension n−1, while these images can also be in parallel generated in the z-direction with the high resolution or a lower resolution by additionally turning on or by turning off the STED-beam, respectively. In total, it is possible to generate simultaneously 4 separate data streams generating the following sets of data:

i) 3-dimensional data set (SPIM) at a high resolution, but imaging a smaller volume of the object;
ii) 3-dimensional data set (SPIM) at a lower resolution, but imaging a larger volume of the object;
iii) 2-dimensional confocal image in z-direction at a high resolution; and
iv) 2-dimensional confocal image in z-direction at a lower resolution.

If only one plane should be illuminated with the light sheet, the following images can be generated simultaneously:

i) 2-dimensional image (SPIM) at a high resolution, but imaging a smaller volume of the object;
ii) 2-dimensional image (SPIM) at a lower resolution, but imaging a larger volume of the object;
iii) 1-dimensional confocal image x-t in z-direction at a high resolution; and
iv) 1-dimensional confocal image x-t in z-direction at a lower resolution.

The number of light sheets in z-direction is not dependent on the x-dimension, i.e. it is possible to choose from different image formats, for instance the number of pixels in x-direction of 512, while the number of pixels in the z-direction can be more or less. For obtaining a continuous data set in the z-direction without gaps, the feed motion in z-direction must be chosen such that always some overlap is guaranteed (Nyquist Theorem).

Figure 9:
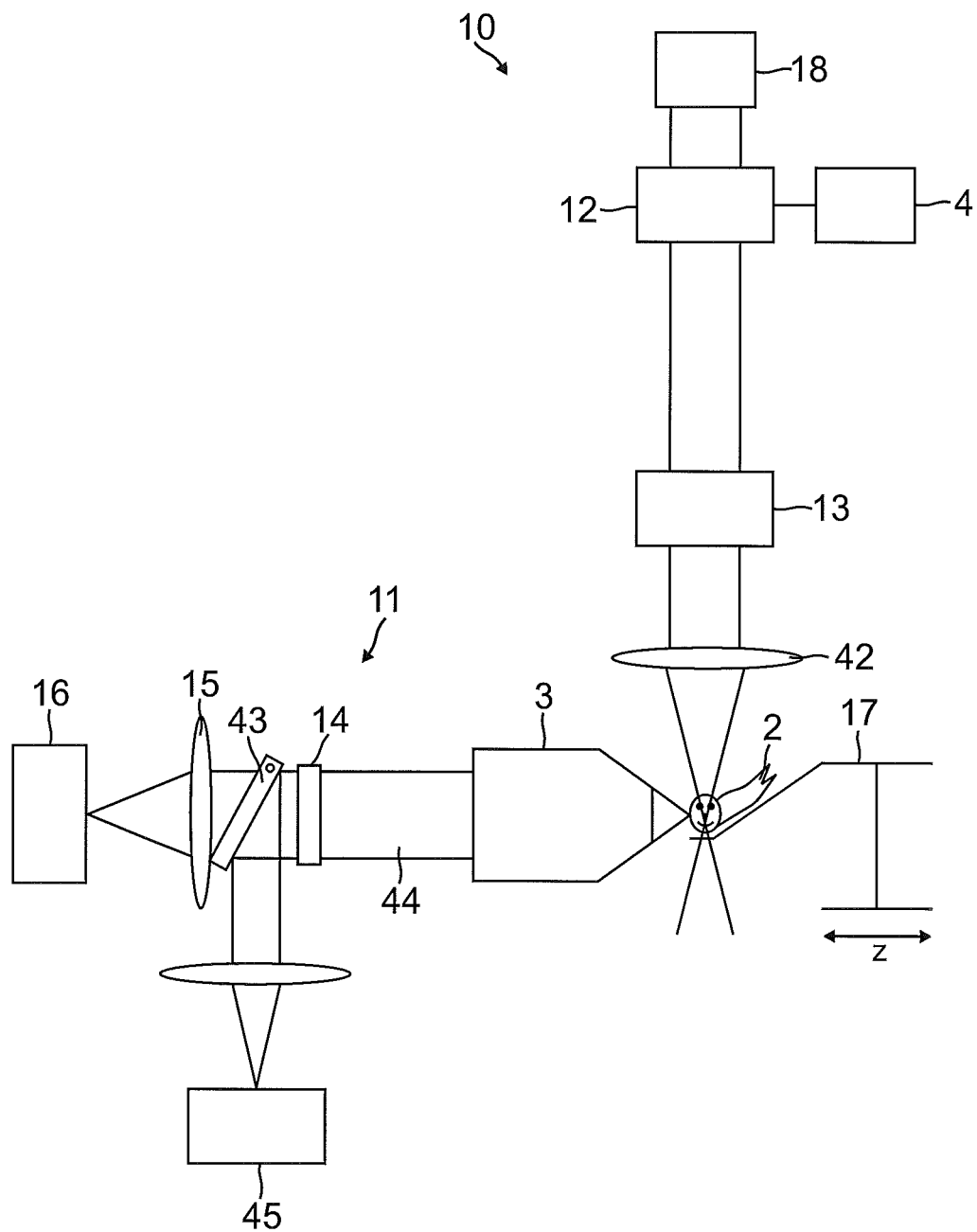
FIG. 9 a schematic view of an additional embodiment of the invention, using the SPIM-detection optics in addition for detecting a multiphoton signal.

FIG. 9 shows an additional embodiment of the invention where the same component parts in comparison to the embodiment according to FIG. 3 are denoted with the same reference numerals. In addition, an illumination objective 42 is provided that can be provided in addition to the zoom optics 13. The illumination objective can also be part of the optical zoom, as for instance in the example according to the embodiment shown in FIG. 4.

In contrast to the illumination with a continuous laser (continuous wave CW) also a pulsed laser can be used for multiphoton fluorescence microscopy sending exciting photons of a long wavelength and of a relatively low energy which is therefore specifically suitable for avoiding damage to the sample, which may particularly be important for biological samples. Like the detection of the SPIM-signal also a multiphoton signal can be extracted by means of a switchable mirror 43 from the detection beam path 44 extending in the z-direction and can be detected by a photomultiplier or an Avalanche photodiode 45. Other than that, the SPIM-signal can be detected by the camera 16 as already described with reference to FIG. 3.

If the camera 16 works fast enough, as a further variation of the embodiment shown in FIG. 9, the switchable mirror 43 can be dispensed with and instead the camera 16 can be used for detecting the multiphoton signal. Since in case of a multiphoton illumination together with detecting the signal in z-direction, i.e. perpendicular to the direction of illumination, for each illumination point on the object a line is imaged onto the camera 16, and by scanning in the x-direction, sequentially a scan-line on the object that extends in the x-direction, an area is sequentially illuminated on the camera 16 that needs to be reduced by software reducing the data back to a line. By scanning in z-direction sequentially several lines of the object can be detected and further processed to an image of an area of the object.

In simple words, this variation of the SPIM signal detection structure is used for a multiphoton signal detection, which is possible with fast cameras, for instance cameras that can detect up to 1000 images per second in the format 512×512.

A specific advantage of the SPIM signal detection structure for the multiphoton signal detection is a significantly increased signal strength, among other reasons due to the following reasons: For generating light sheets typically illumination objectives of a low numerical aperture are used, for instance objectives with a numerical aperture in the range of 0.04 NA. If now the SPIM detection path is used for detecting generated signals from the multiphoton illumination, significantly higher signal strengths can be obtained since the used objectives provide for a much higher numerical aperture (NA) (for instance 1.0 NA). This means gaining signal strength by more than a factor 20.

If the SPIM detection beam path (in z-direction) is used for detecting fluorescent light and the light is sent to a photomultiplier or an APD or APD array or according to the variation described above directly sent to a fast camera, a much higher efficiency can be reached as by using the illumination optics for signal detection in the y-direction, since typically the used numerical aperture of the illumination system is lower than the numerical aperture of the detection system of the SPIM arrangement.

Using multiphoton detection has several advantages. Almost exclusively only those fluorochromes are excited that are in the focus, since excitation requires several photons to arrive more or less simultaneously, which happens almost exclusively in the focus, or put in other words, the likelihood of exciting outside the focus is very low. Another advantage is the higher penetration depth when using wavelengths in the IR range (scattering is low). Another advantage is that no pinhole is necessary, since the entire emitted light can be allocated to the illumination focus. This allows also collecting light from all directions. In contrast, confocal microscopes require that scattered and deflected light needs to be suppressed, which reduces the signal strength. Apart from all these advantages in having a higher signal strength the illumination intensity is lower and therefore avoids damage to the sample, while this solution further provides the structural advantage that the already provided for detection optics of the SPIM-microscope can be used for the multiphoton signal detection, allowing all these advantages without further structural expenditure and only relatively low expenditure on software.

The STED-technology can further also be used for the multiphoton illumination, allowing reducing a resolution of about 300 nm in the multiphoton mode to be reduced to a resolution of only a few nm in the multiphoton-plus-STED mode.

From a software perspective, it is also possible to separate the data detected by the camera 16 into lines and pixels and to generate simultaneously a SPIM image and a multiphoton image. This allows dispensing with switching between SPIM mode and multiphoton mode, or in the alternative the simultaneous operation in the SPIM mode and in the multiphoton mode can be added as a switching option.

Summarizing, the microscope according to the invention applies a partial aspect of confocal microscopy, namely the partial aspect of the illumination optics, for generating an image based on the SPIM-technology, wherein the illumination optics is further modified to a zoom optics, and according to the invention further a confocal image can be generated that is one dimension lower than the image generated by the SPIM technology, or in the alternative in addition to the confocal image a multiphoton image can be generated, also in lieu of the image generated by the SPIM technology. This does not only allow to influence the image generated by the SPIM technology much more flexibly but allows also for additional image information obtained confocally or by multiphoton detection, and depending on the specific application, the resulting images can also be combined as an overlay with the SPIM and/or the multiphoton images. By adding or by turning off a STED beam the image can be influenced further and it is possible to generate even additional data streams for a variety of images, which further have the advantage of being generated simultaneously. This allows for providing the microscope with a manifold utility with synergistic effects in the possibilities of modulating the image and at the same time in the number of analyzable image information.

What is claimed is:

1. A SPIM-microscope comprising:
    a light source sending an illumination light beam from a y-direction onto an object to be imaged;
    a camera detecting in a z-direction as a first detection direction light emanating from the object as at least one of fluorescent light and reflected light, wherein the z-direction extends substantially perpendicular to the y-direction;
    an x-scanner generating a sequential light sheet by scanning the illumination light beam in an x-direction, wherein the x-direction extends substantially perpendicular to the y-direction and to the z-direction and the light sheet is sequentially formed in a plane that is defined by the x-direction and the y-direction;
    a photodetector detecting fluorescent light as a detection light sent from the object in an opposite direction of the y-direction as a second detection direction; and
    a switch adapted to switch between the following operational modes: confocal detection of detection light opposite to the y-illumination direction; SPIM-detection of wide field detection light in the z-direction; and simultaneous detection of the aforementioned confocal detection and SPIM-detection.

2. The SPIM-microscope according to claim 1, wherein in parallel to a 2-dimensional wide field image generated by a SPIM-technology also confocally a 1-dimensional image of the object is generated that comprises a line extending in the x-direction.

3. The SPIM-microscope according to claim 1, wherein the camera is an area detector chosen from the group consisting of CMOS-camera, CCD-camera or array-detectors.

4. The SPIM-microscope according to claim 1, further comprising an electronic zoom adapted to change a scanning length in the x-direction.

5. The SPIM-microscope according to claim 4, wherein a number of image pixels in x-direction is maintained unchanged by the electronic zoom independently of the scanning length in x-direction that has been selected.

6. The SPIM-microscope according to claim 1, wherein the illumination light beam scanned in the x-direction is turned off at or close to a return point where a maximum scanning length in x-direction has been reached.

7. The SPIM-microscope according to claim 1, further comprising an illumination optics comprising a zoom optics provided in a beam path of the illumination light beam, the zoom optics being adapted to change a focal length of the illumination light beam.

8. The SPIM-microscope according to claim 7, wherein the zoom optics that are adapted to vary the focal length of the illumination light beam is an optical zoom having lens groups which are mechanically moved with respect to each other.

9. The SPIM-microscope according to claim 8, wherein the zoom optics are adapted to expand or shorten the focal length of the illumination light beam by changing a numerical aperture and therefore expand or shorten a length of a field in the y-illumination direction that is illuminated by the light sheet.

10. The SPIM-microscope according to claim 1, further comprising a first z-scanner moving the object in the z-direction so that sequentially a plurality of light sheets spaced in z-direction with respect to each other are generated in respective illumination planes, wherein a distance between respective light sheets and the camera remains unchanged.

11. The SPIM-microscope according to claim 10, further comprising an electronic zoom by which a scanning length in the z-direction can be changed along which a plurality of spaced apart light sheets are generated sequentially.

12. The SPIM-microscope according to claim 10, further comprising an image processing unit that combines sequentially generated images correlating to the plurality of light sheets which are spaced in the z-direction in a distance to each other into a 3-dimensional image.

13. The SPIM-microscope according to claim 12, further comprising a photodetector detecting detection light sent from the object in an opposite direction of the y-direction as a second detection direction, the detection light being at least one of fluorescent light and reflected light, wherein in parallel to the 3-dimensional image generated by a SPIM-technology also confocally a 2-dimensional image of the object is generated in a plane defined by the x-direction and the z-direction.

14. The SPIM-microscope according to claim 1, further comprising:
    a second z-scanner moving the illumination light beam in the z-direction in relation to the object for generating sequentially a plurality of light sheets spaced in the z-direction with respect to each other; and
    a third z-scanner that tracks a detection beam path according to a deflection of the illumination light beam in z-direction by the second z-scanner so that a distance between the light sheet and the camera remains unchanged.

15. The SPIM-microscope according to claim 14, further comprising an image processing unit that combines sequentially generated images correlating to the plurality of light sheets which are spaced in the z-direction in a distance to each other to a 3-dimensional image.

16. The SPIM-microscope according to claim 15, further comprising a photodetector detecting detection light sent from the object in an opposite direction of the y-direction as a second detection direction, the detection light being at least one of fluorescent light and reflected light, wherein in parallel to the 3-dimensional image generated by a SPIM-technology also confocally a 2-dimensional image of the object is generated in a plane defined by the x-direction and the z-direction.

17. The SPIM-microscope according to claim 1, wherein a number of light sheets which are spaced with respect to each other in the z-direction is maintained unchanged by an electronic zoom independently of a scanning length in the z-direction that has been selected.

18. The SPIM-microscope according to claim 1, wherein
the illumination light source is a pulsed laser;
the illumination light beam is a multiphoton laser beam; and
a multiphoton signal is detected in the z-direction.

19. The SPIM-microscope according to claim 18, wherein the camera is a fast camera that is adapted to detect in addition to the SPIM signal also the multiphoton signal.

20. The SPIM-microscope according to claim 18, further comprising a switchable mirror allowing extracting the multiphoton signal from the z-direction and directing it to a photodetector.

21. The SPIM-microscope according to according to claim 1, further comprising a deactivation light source sending from the y-direction a deactivation light beam onto the object making the sequentially generated light sheet in the z-direction thinner, wherein the deactivation light beam is sent offset in the z-direction onto the object in relation to the illumination light beam and extends in parallel to that illumination light beam that is scanned in the x-direction.

22. The SPIM-microscope according to claim 21, further comprising an excitation light beam modulator adapted to modulate the excitation light beam into a Besse beam.

* * * * *

UNITED STATES PATENT AND TRADEMARK OFFICE
CERTIFICATE OF CORRECTION

| | |
|---|---|
| PATENT NO. | : 9,057,879 B2 |
| APPLICATION NO. | : 13/278986 |
| DATED | : June 16, 2015 |
| INVENTOR(S) | : Werner Knebel and Wolfgang Oestreicher |

It is certified that error appears in the above-identified patent and that said Letters Patent is hereby corrected as shown below:

In the claims

Claim 22 reads:

The SPIM-microscope according to claim 21, further comprising an excitation light beam modulator adapted to modulate the excitation light beam into a Besse beam.

And should read:

The SPIM-microscope according to claim 21, further comprising an excitation light beam modulator adapted to modulate the excitation light beam into a Bessel beam.

Signed and Sealed this
Twenty-ninth Day of December, 2015

Michelle K. Lee
*Director of the United States Patent and Trademark Office*